(12) United States Patent
Dakka et al.

(10) Patent No.: US 8,658,834 B2
(45) Date of Patent: Feb. 25, 2014

(54) HYDROGENATION PROCESS

(75) Inventors: Jihad M. Dakka, Whitehouse Station, NJ (US); Keith H. Kuechler, Friendswood, TX (US); James R. Lattner, Laporte, TX (US); Edmund J. Mozeleski, Califon, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/516,414

(22) PCT Filed: Nov. 23, 2010

(86) PCT No.: PCT/US2010/057753
§ 371 (c)(1),
(2), (4) Date: Jul. 20, 2012

(87) PCT Pub. No.: WO2011/100013
PCT Pub. Date: Aug. 18, 2011

(65) Prior Publication Data
US 2012/0277472 A1    Nov. 1, 2012

Related U.S. Application Data

(60) Provisional application No. 61/304,040, filed on Feb. 12, 2010.

(51) Int. Cl.
*C07C 37/06* (2006.01)
*C07C 2/76* (2006.01)

(52) U.S. Cl.
USPC .......................... 568/366; 568/376; 568/798

(58) Field of Classification Search
USPC ................................... 568/366, 798
See application file for complete search history.

(56) References Cited

U.S. PATENT DOCUMENTS

| 4,169,857 A | 10/1979 | Murtha |
| 5,292,960 A | 3/1994 | Meier et al. |
| 6,037,513 A | 3/2000 | Chang et al. |
| 7,199,271 B2 | 4/2007 | Fodor |

FOREIGN PATENT DOCUMENTS

| WO | 2008/101616 | 8/2008 |
| WO | 2009/038900 | 3/2009 |
| WO | 2010/024975 | 3/2010 |

*Primary Examiner* — Sikarl Witherspoon
(74) *Attorney, Agent, or Firm* — Jamie L. Sullivan; Siwen Chen

(57) ABSTRACT

The present invention relates to a hydrogenation process that may be used in connection with the production of phenol. In the process, a composition comprising: (i) cyclohexylbenzene; and (ii) a hydrogenable component are contacted with hydrogen in the presence of a hydrogenation catalyst under hydrogenation conditions. The hydrogenable component can be one or more of an olefin, a ketone or phenol. The hydrogenation catalyst has hydrogenation component and a support.

26 Claims, 5 Drawing Sheets

HYDROGENATION PROCESS

PRIORITY CLAIM

This application is a National Stage Application of International Application No. PCT/US2010/057753 filed Nov. 23, 2010, which claims priority to U.S. Provisional Application Ser. No. 61/304,040 filed Feb. 12, 2010, the disclosures of which are fully incorporated herein by their reference.

FIELD

The present invention relates to a hydrogenation process. More particularly, the invention relates to a hydrogenation process that may be used in the production of phenol.

BACKGROUND

Various processes can be used to make phenol. For example, phenol can be made by the Hock process, which involves alkylation of benzene with propylene to produce cumene, oxidation of the cumene to the corresponding hydroperoxide, and cleavage of the hydroperoxide to produce phenol and acetone.

Phenol can also be made by alkylation of benzene and a $C_4$ alkylating agent to produce sec-butylbenzene, oxidation of the sec-butylbenzene to sec-butylbenzene hydroperoxide, and cleavage of the sec-butylbenzene hydroperoxide to produce phenol and methyl ethyl ketone.

Another process for making phenol involves hydroalkylation of benzene to produce cyclohexylbenzene, oxidation of the cyclohexylbenzene to cyclohexylbenzene hydroperoxide, and cleavage of the cyclohexylbenzene hydroperoxide to produce phenol and cyclohexanone.

However, one or more steps of the processes described above can produce substances that are detrimental to process efficiency. For example, and as illustrated in FIG. 1A (with reference to Example 1), the inventors have discovered that the presence of olefins, such as those produced in the hydroalkylation/alkylation and cleavage steps described above, can interfere with oxidation and result in slower conversion and reduced selectivity to the corresponding hydroperoxide.

Additionally, and as illustrated in FIG. 1B (with reference to Example 2), the inventors have discovered that phenol and phenolics, which may be present in one or more recycle streams of a process for making phenol, can also interfere with oxidation.

That said, many of these substances have boiling points very close to those of cumene, sec-butylbenzene and cyclohexylbenzene, making them difficult to separate by conventional techniques, such as distillation.

As such, what is needed is a process for treating such substances to make them substantially inert relative to, more easily separable from, and/or directly remove them from, phenol production processes.

SUMMARY

The invention relates to a hydrogenation process in which a composition comprising: (i) greater than about 50 wt % of cyclohexylbenzene, the wt % based upon total weight of the composition; and (ii) a hydrogenable component is contacted with hydrogen in the presence of a hydrogenation catalyst under hydrogenation conditions.

The invention also relates to a hydrogenation process in which a composition having: (i) cyclohexylbenzene; and (ii) a hydrogenable component selected from at least one of an olefin, ketone and/or phenol with hydrogen in the presence of a hydrogenation catalyst under hydrogenation conditions, wherein the conversion of the hydrogenable component is at least 50% more selective to form cyclohexylbenzene than bicyclohexane.

The invention also relates to a hydrogenation and oxidation process in which a feed comprising cyclohexenylbenzene is contacted with hydrogen in the presence of a hydrogenation catalyst under hydrogenation conditions to form cyclohexylbenzene. The cyclohexylbenzene is then reacted with oxygen (e.g., air) in the presence of an oxidation catalyst under oxidation conditions to form cyclohexylbenzene hydroperoxide.

The invention also relates to a process for producing phenol comprising: (i) hydroalkylating benzene to form a composition having: (1) cyclohexylbenzene; and (2) a hydrogenable component; (ii) hydrogenating at least a portion of the hydrogenable component; (iii) oxidizing the cyclohexylbenzene to form an oxidized composition comprising a hydroperoxide; and (iv) cleaving the hydroperoxide to form phenol and/or cyclohexanone.

DETAILED DESCRIPTION OF THE EMBODIMENTS

Figure 1A:
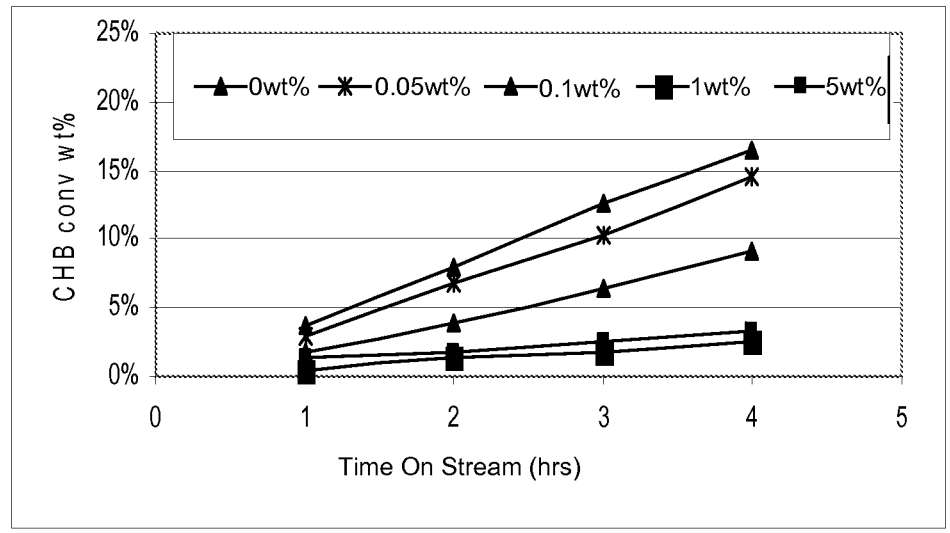
FIG. 1A shows Time On Stream (T.O.S.) vs. CHB conversion of a composition having varying amounts of olefins during oxidation.

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention can be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

That said, described herein is a hydrogenation process. This process may be conducted alone, or in conjunction with one or more steps of a process to produce phenol, such as: (i)

alkylation and/or hydroalkylation; (ii) oxidation; (iii) cleavage; and/or (iv) dehydrogenation.

Hydrogenation Process

In accordance with various embodiments, the hydrogenation process comprises contacting a composition having: (i) a first component; and (ii) a second component with hydrogen in the presence of a hydrogenation catalyst under hydrogenation conditions.

The first component can be any substance that is present in a process for making phenol. In one embodiment, the first component is cumene, sec-butylbenzene (SBB), cyclohexylbenzene (CHB), or methylcyclopentyl benzene. In various embodiments, the composition comprises greater than about 50 wt % of the first component, or greater than about 60 wt % of the first component, based upon total weight of the composition. The first component may be may be supplied from any source. For example, it may be supplied from a fresh source, produced during alkylation or hydroalkylation, and/or recycled from a step in the phenol production process.

The second component (also referred to as a "hydrogenable component") can be any substance that can react with hydrogen. For example, a hydrogenable component may have one or more of an unsaturated double bond or triple bond, a hydroxyl group, and a carbonyl group. The hydrogenable component may have a cyclic group. In one embodiment, the cyclic group is aromatic.

In various embodiments, the composition comprises greater than about 0.01 wt % of a hydrogenable component, or greater than about 0.1 wt % of a hydrogenable component, or greater than about 1 wt % of a hydrogenable component, based upon total weight of the composition. In various embodiments, the hydrogenable component is made during one or more of alkylation/hydroalkylation, oxidation, cleavage and dehydrogenation steps.

In an embodiment, the hydrogenable component is an olefin. For example, the hydrogenable component can be an olefin made during alkylation or hydroalkylation of benzene to produce cumene, SBB or CHB. Exemplary olefins include, but are not limited to, phenyl cyclohexene, phenylbutene, phenyl methyl cyclopentene, butene, cyclohexene, methylcyclopentene, methylcyclopentenylbenzene, phenymethylcyclopenes, higher olefin oligomers (>C8+), phenyl propylene, α-methylstyrene, α-ethylstyrene, butenyl-benzene and cyclopentene.

Figure 2:
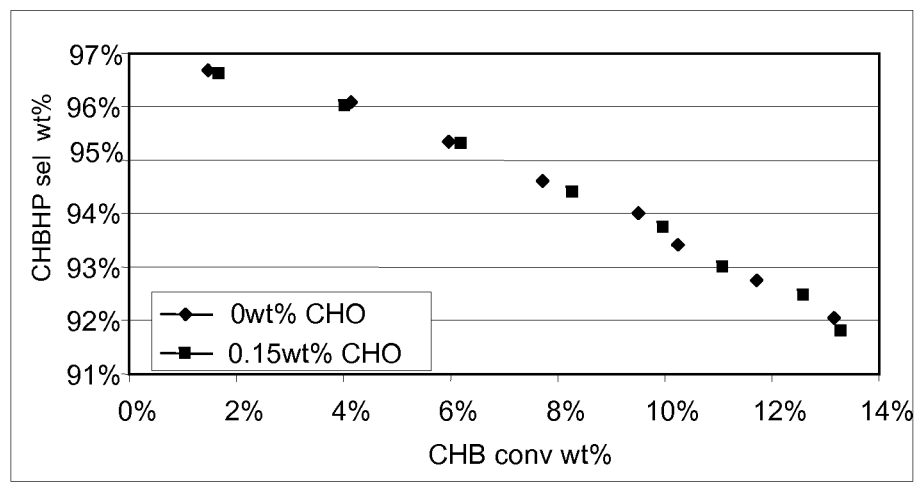
FIG. 2 shows CHB conversion vs. cyclohexylbenzene hydroperoxide (CHBHP) selectivity of a composition having varying amounts of cyclohexanone during oxidation.

In an embodiment, the hydrogenable component is phenol. For example, the hydrogenable component may comprise phenol produced during cleavage of cumene, SBB or CHB peroxide. Hydrogenation of phenol may be desirable, for example, when it is present in a composition that will be recycled to the oxidation step of a phenol process. In particular, the inventors have discovered that hydrogenation of phenol under the hydrogenation conditions described herein produces at least one of cyclohexanone and/or cyclohexanol (by way of the reactions shown below). As shown in FIG. 2 (with reference to Example 3), the presence of cyclohexanone does not substantially impact selectivity to hydroperoxide during oxidation.

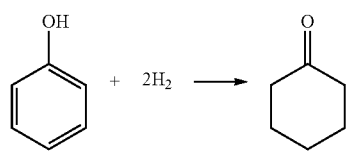

-continued

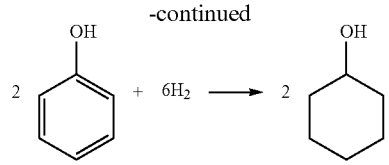

In an embodiment, the hydrogenation process hydrogenates the phenol prior to the oxidation step such that composition comprises less than about 1 wt % phenol, or less than about 0.5 wt % phenol, or less than about 0.1 wt % phenol, based upon total weight of the composition.

In an embodiment, the hydrogenable component is a ketone. For example, hydrogenable component may be a ketone produced during oxidation and/or dehydrogenation steps. Exemplary ketones include, but are not limited to, phenylbutanone, phenylcyclopentanone, phenylmethylcyclopentanone, benzene cyclohexeneone, cyclohexyllidine, cyclohexanone, acetophenone, methylphenylcyclopentanone, 6-hydroxyhexaphenone, cyclohexylcyclohexanone, and phenylcyclohexanone.

Figure 4:
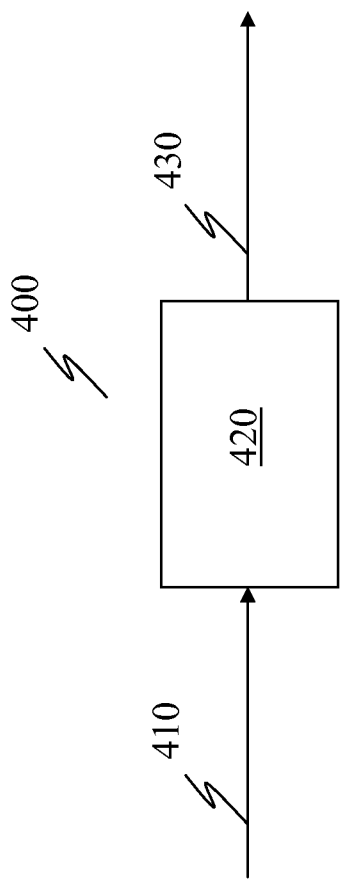
FIG. 4 illustrates an embodiment of a hydrogenation process.

By way of illustration, FIG. 4 shows an embodiment of a hydrogenation process 400. Composition 410 comprises a first component and a hydrogenable component and is supplied to reactor 420 where it is contacted with hydrogen and a hydrogenation catalyst under hydrogenation conditions to form composition 430, which has less of the hydrogenable component.

In various embodiments, the hydrogenation process described herein produces a composition comprising less than about 1 wt %, or less than about 0.1 wt %, or less than about 0.01 wt % of the hydrogenable component, based upon total weight of the composition.

It will be understood that the hydrogenation process may be carried out as a batch process, semi-batch process or continuous process.

The hydrogen may be introduced to the hydrogenation process from any source. For example, fresh hydrogen may be used, or hydrogen may be obtained from one or more recycle streams of a phenol production process.

The hydrogenation catalyst may be any catalyst that can facilitate hydrogenation. In an embodiment, the catalyst comprises: (i) a hydrogenation component; and (ii) a support.

The hydrogenation component may comprise at least one metal component selected from Groups 6 to 10 of the Periodic Table of Elements, such as platinum, palladium and compounds and mixtures thereof. The hydrogenation component may be present in an amount between about 0.1 and about 10 wt %, or about 0.2 to about 0.5 wt %, or about 0.3 wt %, wherein the wt % is based upon total weight of the hydrogenation catalyst.

The term "metal component" is used herein to include a metal compound that may not be purely the elemental metal, but could, for example, be at least partly in another form, such as an oxide, hydride or sulfide form. The weight % (wt %) of the metal component is herein defined as being measured as the metal present based on the total weight of the catalyst composition irrespective of the form in which the metal component is present.

The support may comprise one or more of aluminum oxide, silica, silicate, aluminosilicates including but not limited to zeolytes and MCM-41, carbon, and a carbon nanotube. Impurities may also be present in the support. For example, sodium salts such as sodium silicate can be present from anywhere from about 0.01 to about 2 wt % based upon total weight of the hydrogenation catalyst.

The hydrogenation conditions may be any conditions suitable to cause the hydrogenable component to react with hydrogen. In various embodiments, the hydrogenation conditions comprise a pressure of about 0 kPa,g (kPa, gauge) to about 3450 kPa,g, or about 500 kPa,g to about 2000 kPa,g, or about 750 kPa,g to about 1500 kPa,g, or about 1000 kPa,g and a temperature of about 10° C. to about 100° C., or about 40° C. to about 80° C., or about 65° C.

In accordance with one aspect of the invention, it has been advantageously discovered that the use of the hydrogenation conditions and hydrogenation catalyst disclosed herein results in selective hydrogenation of olefins and ketones without substantially affecting aromatic groups. For example, cyclohexenylbenzene is selectively converted to CHB rather than bicyclohexane:

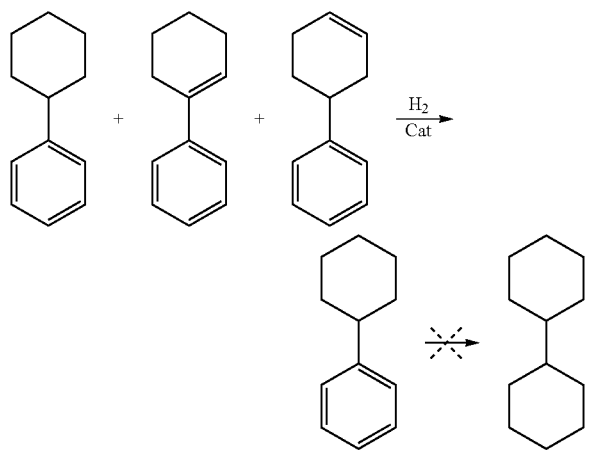

Similarly, phenylcyclohexanone is converted to CHB rather than bicyclohexane:

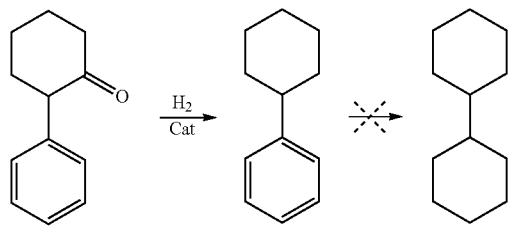

In various embodiments, the conversion of the hydrogenable component is at least 50%, or 60%, or 70% more selective to CHB than to bicyclohexane, or SBB than to butylcyclohexane, respectively. In various embodiments, the hydrogenation process produces less than about 1 wt %, or less than about 0.5 wt %, or less than 0.05 wt % bicyclohexane or butylcyclohexane, the wt % s based upon total weight of the composition.

The hydrogenation process may be performed as a stand-alone process or as part of a process to produce phenol. For example, the hydrogenation process may be performed in any sequence with one or more of the steps of: (a) alkylation or hydroalkylation; (b) oxidation; (c) cleavage; and (d) dehydrogenation. These steps are described in more detail below.

Alkylation/Hydroalkylation

As discussed above, the hydrogenation process may be part of a process to produce phenol that includes alkylation or hydroalkylation of benzene.

In one embodiment, alkylation involves alkylating benzene and propylene to form cumene. In another embodiment, alkylation involves alkylating benzene with a $C_4$ alkylating agent over an acid catalyst to form SBB. Examples of suitable $C_4$ alkylating agents include mono-olefins, such as linear butenes, particularly butene-1 and/or butene-2; alcohols (inclusive of monoalcohols, dialcohols, trialcohols, etc.) such as the butanols; dialkyl ethers, such as dibutyl ethers; and alkyl halides such as the butyl chlorides.

In one embodiment, benzene is alkylated with cyclohexene in the presence of an acid catalyst, such as zeolite beta or an MCM-22 family molecular sieve, or by oxidative coupling of benzene to biphenyl followed by hydrogenation of the biphenyl. In another embodiment, alkylation involves hydroalkylating benzene with hydrogen under hydroalkylation conditions in the presence of a hydroalkylation catalyst whereby the benzene undergoes the following reaction to produce CHB:

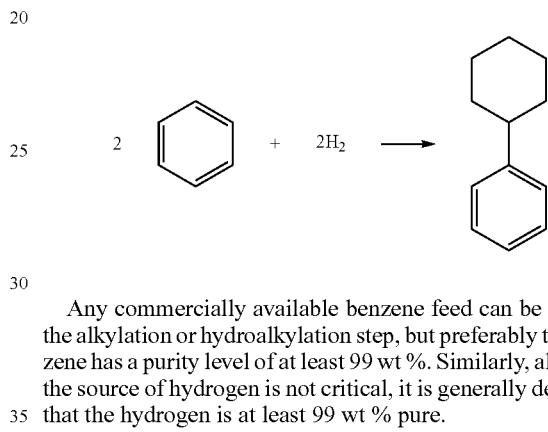

Any commercially available benzene feed can be used in the alkylation or hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the alkylation or hydroalkylation step contains less than 500 ppm, or less than 100 ppm, or about 12-20 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The alkylation or hydroalkylation reaction can be conducted in a wide range of reactor configurations including fixed bed, slurry reactors, and/or catalytic distillation towers. In addition, the reaction can be conducted in a single reaction zone or in a plurality of reaction zones, in which at least the hydrogen is introduced to the reaction in stages. In one embodiment, hydrogen addition or benzene addition can be staged with internal recycle for cooling. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst used in the alkylation or hydroalkylation reaction may be a bifunctional catalyst comprising a MCM-22 family molecular sieve and a hydrogenation metal. The MCM-22 family molecular sieve includes:
  molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth Edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof Preferably, the molecular sieve is selected from (a) EMM-10, (b) EMM-11, (c) EMM-12, (d) EMM-13, (e) MCM-49, (f) MCM-56 and (g) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In one embodiment, the hydrogenation metal is supported on an inorganic oxide.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), p. 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed.

Oxidation

The hydrogenation process may be conducted as part of a process that includes oxidation (e.g., cumene oxidation, SBB oxidation, and CHB oxidation or mixtures thereof).

Oxidation may be accomplished by introducing an oxygen-containing gas, such as air or enriched air into a liquid phase. The oxidation may be conducted in the presence or absence of a catalyst.

Suitable catalysts for the oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between about 0.0001 mol % to about 15 wt %, such as between about 0.001 to about 5 wt %, of the cumene, SBB or CHB.

Suitable oxidation conditions include a temperature between about 70° C. and about 200° C., such as about 90° C. to about 130° C., and a pressure of about 50 to about 10,000 kPa. Any oxygen-containing gas, preferably air, can be used as the oxidizing medium. The reaction can take place in batch reactors or continuous flow reactors. In one embodiment, the acids generated during oxidation are in the off gas streams and are neutralized with caustic (e.g., sodium carbonate) and separated or eliminated with the use of equipment such as chillers, decanter drums and adsorbers. The aqueous effluent from the oxidizers may then be neutralized and sent to waste water.

Cleavage

The hydrogenation process may be conducted as part of a process that includes peroxide cleavage (e.g., cumene peroxide, SBB peroxide, or CHB peroxide cleavage).

Cleavage of the peroxide can be effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The hydroperoxide is preferably diluted in an organic solvent inert to the cleavage reaction, such as methyl ethyl ketone (MEK), cyclohexanone, phenol or CHB, to assist in heat removal. The cleavage reaction is conveniently conducted in a series of heat exchangers, one or more well mixed reaction vessels, or a catalytic distillation unit.

The catalyst employed in the cleavage step can be a homogeneous catalyst or a heterogeneous catalyst. Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of about 0.05 to about 0.5 wt %. For a homogeneous acid catalyst, a neutralization step preferably follows the cleavage step. Such a neutralization step typically involves contact with a basic component, with subsequent decanting of a salt-enriched aqueous phase.

Any suitable heterogeneous catalyst may be used, such as those described in U.S. Pat. No. 4,870,217, which is incorporated by reference for this purpose.

Dehydrogenation

The hydrogenation process may be conducted as part of a process that includes dehydrogenation of a ketone that is made during the production of phenol (e.g., acetone, MEK or cyclohexanone). Dehydrogenation generally involves contacting the ketone with a dehydrogenation catalyst.

The catalyst may comprise: (i) a support; (ii) a first component; and (iii) a hydrogenable component produced such that the catalyst exhibits an oxygen chemisorption of greater than 0.5, preferably greater than 0.6 and more preferably greater than 0.7.

Conveniently, the support employed in the dehydrogenation catalyst is selected from the group consisting of silica, a silicate, an aluminosilicate such as including zeolytes and MCM-41, zirconia, carbon and carbon nanotubes, and preferably comprises silica. Impurities which can be present in the catalyst support (e.g., silica) are, for example, sodium salts such as sodium silicate which can be present from anywhere from about 0.01 to about 2 wt %.

Generally, the first component employed in the present catalyst comprises at least one metal selected from Groups 6 to 10 of the Periodic Table of Elements and compounds and mixtures thereof, such as platinum, palladium and compounds and mixtures thereof In another embodiment, the first component comprises at least one metal selected from Group 10 of the Periodic Table of Elements and compounds and mixtures thereof Typically, the first component is present in an amount between about 0.1 and about 10 wt % of the catalyst.

In addition, the catalyst comprises a second component comprising at least one metal or compound thereof selected from Group 1 and Group 2 of the Periodic Table of Elements wherein, said at least one metal or compound thereof selected from Group 1 and Group 2 of the Periodic Table of Elements is present in an amount of at least 0.1 wt %, at least 0.2 wt %, at least 0.3 wt %, at least 0.4 wt % and at least 0.5 wt %. In one embodiment, the second component comprises at least one metal or compound thereof selected from Group 1 of the Periodic Table of Elements, such as potassium, cesium and rubidium and compounds and mixtures thereof; preferably potassium and potassium compounds. In another embodiment, the second component comprises at least one metal or compound thereof selected from Group 1 or 2 of the Periodic Table of Elements. Typically, the second component is present in an amount between about 0.1 and about 5 wt % of the catalyst.

Suitable conditions for the dehydrogenation step include a temperature of about 250° C. to about 750° C., a pressure of about atmospheric to about 500 psi-gauge (psig) [100 to 3447 kPa-gauge (kPa,g)], a weight hourly space velocity of about 0.2 to about 50 hr$^{-1}$, and a hydrogen to cyclohexanone-containing feed molar ratio of about 0 to about 20.

The temperature of the dehydrogenation process may be from about 300° C. to about 750° C. and from about 400° C. to about 500° C.

The pressure of the dehydrogenation process may be from about 0 to about 300 psig (0 to 2068 kPa,g) or from about 100 to about 300 psig (689 to 2068 kPa,g).

The reactor configuration used for the dehydrogenation process generally comprises one or more fixed bed reactors containing a solid catalyst with a dehydrogenation function.

In one embodiment, separation can be enhanced by conducting the distillation under at least partial vacuum, typically at below 101 kPa. Moreover, extractive distillation processes are known. See for example, U.S. Pat. Nos. 4,021,490; 4,019,965; 4,115,207; 4,115,204; 4,115,206; 4,201,632; 4,230,638; 4,167,456; 4,115,205; and 4,016,049.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The first separation step is conveniently effected by vacuum distillation and the same, or additional vacuum distillation steps, can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

By employing the present dehydrogenation process, substantially all the ketone can be converted to phenol. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

Exemplary Processes

Figure 5:
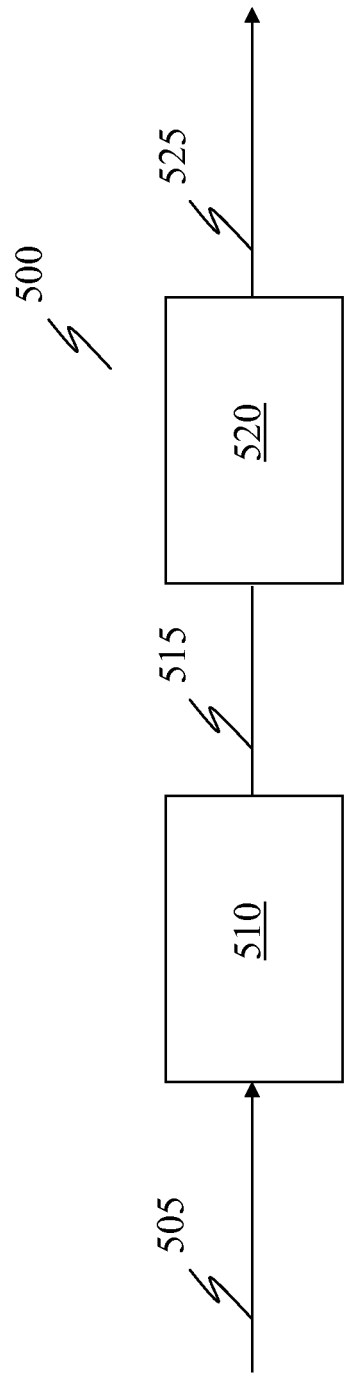
FIG. 5 illustrates an embodiment of a process for producing a hydroperoxide.

FIG. 5 illustrates phenol process 500 comprising Step 510: hydrogenating composition 505 comprising a first component and a hydrogenable component in the presence of a hydrogenation catalyst under hydrogenation conditions to form composition 515; and Step 520: oxidizing the first component in composition 515 in the presence of an oxidation catalyst under oxidation conditions to form composition 525 comprising a peroxide or hydroperoxide.

Figure 6:
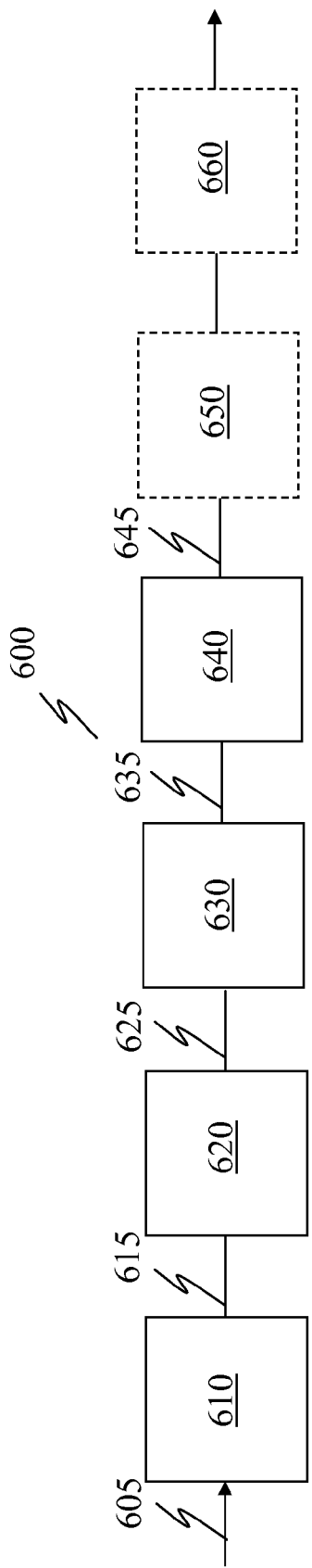
FIG. 6 illustrates an embodiment of a process for producing phenol.

In the embodiment illustrated in FIG. 6, phenol process 600 comprises Step 610: alkylating or hydroalkylating benzene feed 605 to form composition 615 comprising first component and a hydrogenable component; Step 620: hydrogenating at least a portion of the hydrogenable component to form composition 625; Step 630: oxidizing at least a portion of the first component in composition 625 to form composition 635 comprising a peroxide; and Step 640: cleaving the peroxide in the composition 635 to form composition 645 comprising phenol and a ketone (e.g., acetone, MEK or cyclohexanone). Optionally, system 600 may further comprise one or more additional steps, such as Step 650: hydrogenating at least a portion of any hydrogenable component that is present in composition 645; and/or Step 660: dehydrogenating the ketone.

Figure 7:
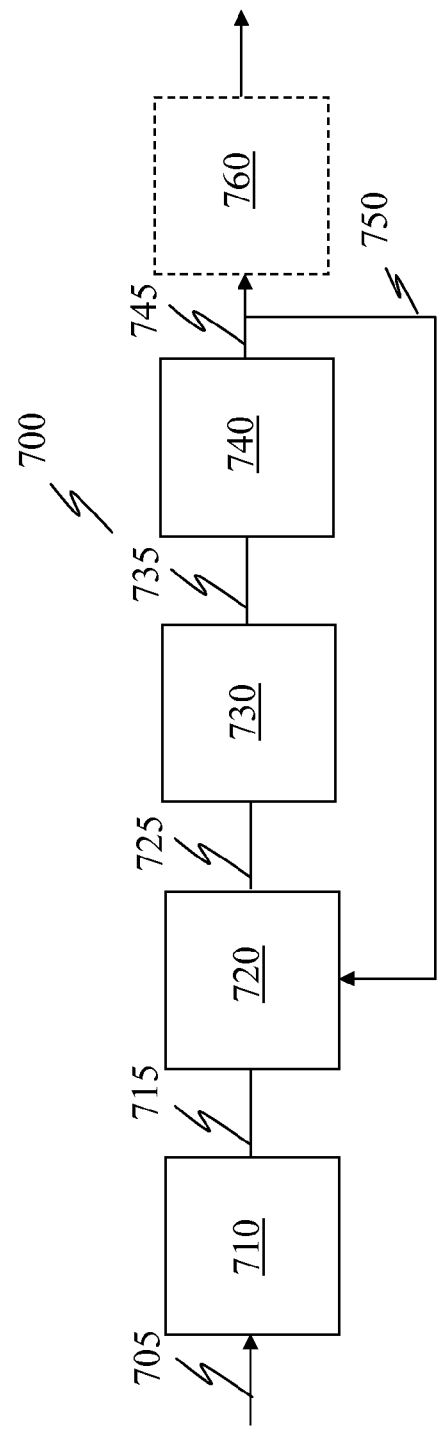
FIG. 7 illustrates an embodiment of a process for producing phenol comprising a recycle to the hydrogenation process.

In various embodiments, hydrogenable components produced in different steps of a phenol process are hydrogenated in a single step. For example, as illustrated in FIG. 7, phenol process 700 comprises Step 710: alkylating or hydroalkylating feed 705 comprising benzene to form composition 715 comprising a first component and a hydrogenable component; Step 720: hydrogenating at least a portion of the hydrogenable component in composition 715 to form composition 725; Step 730: oxidizing composition 725 to form composition 735 comprising a peroxide; and Step 740: cleaving the peroxide to form composition 745 comprising phenol, a ketone and hydrogenable component; and Step 750: recycling at least a portion of the hydrogenable component in composition 745 to hydrogenating step 720. Optionally, process 700 may further comprise Step 760: dehydrogenating the ketone present in composition 745.

The invention will now be more particularly described with reference to the following non-limiting Examples and the accompanying figures.

Example 1

Effect of Olefins on Oxidation

One hundred and fifty (150) grams of CHB was oxidized in the presence of 5, 1, 0.1, 0.5 and 0 wt % of an olefin (namely, cyclohexenylbenzene) to determine the effect of olefins on CHB conversion. Oxidation was conducted using 0.1 wt % NHPI catalyst at 110° C. and 1 atm. As shown in FIG. 1A, reducing olefin content improves CHB conversion.

Example 2

Effect of Phenol on Oxidation

Figure 1B:
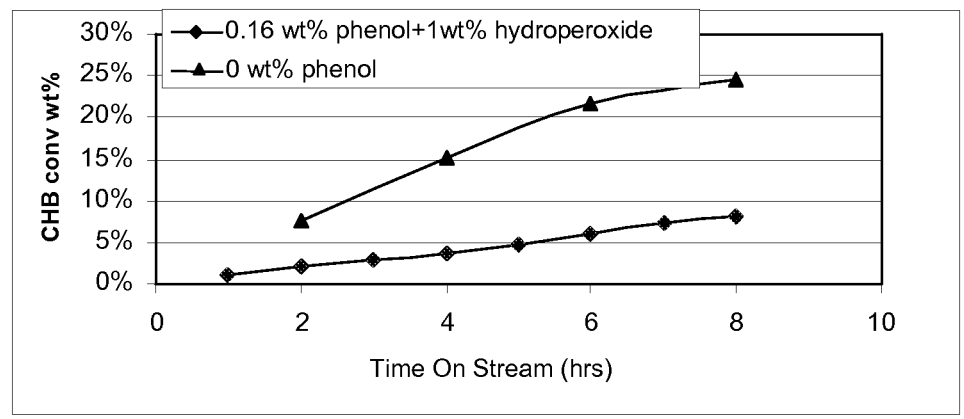
FIG. 1B shows T.O.S. vs. CHB conversion of a composition having varying amounts of phenol during oxidation.

One hundred and fifty (150) grams of CHB was oxidized in the presence of: (i) 0.16 wt % phenol and 1 wt % hydroperoxide (HP); and (ii) 0 wt % phenol to determine the effect of phenol on CHB conversion. Oxidation was conducted using 0.1 wt % NHPI catalyst at 110° C. and 1 atm (101 kPa). As shown in FIG. 1B, reducing phenol content improves CHB conversion.

Example 3

Effect of Cyclohexanone on Oxidation

One hundred and fifty (150) grams of CHB was oxidized in the presence of: (i) 0.15 wt % cyclohexanone (CHO); and (ii) 0 wt % CHO to determine the detrimental effect of cyclohexanone on cyclohexylbenzene hydroperoxide (CHBHP) selectivity. Oxidation was conducted using 0.1 wt % NHPI catalyst at 110° C. and 101 kPa (14.7 psi). As shown in FIG. 2, the presence of cyclohexanone does not significantly affect selectivity to CHBHP.

Example 4

Oxidation

Figure 3:
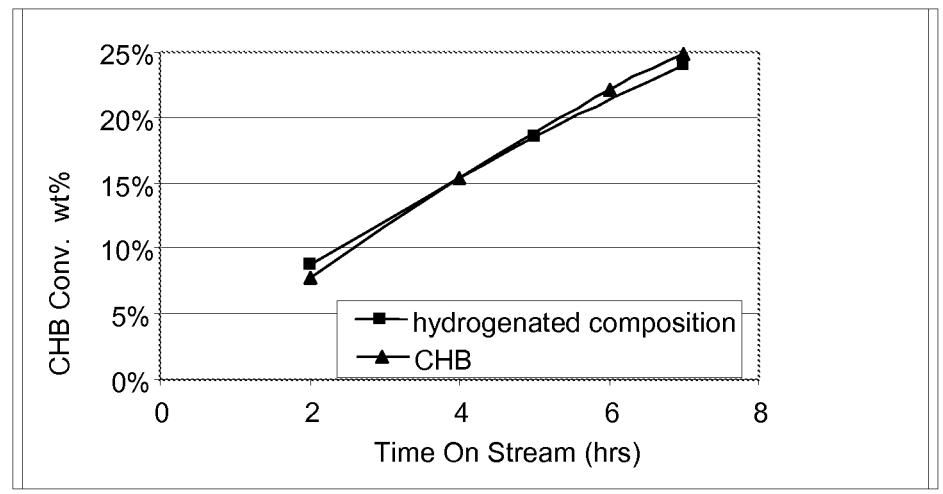
FIG. 3 shows T.O.S. vs. CHB conversion of a hydrogenated composition and pure CHB.

One hundred and fifty (150) grams of a composition comprising CHB and olefins was hydrogenated at 65° C. and 1,000 psi,g to form a hydrogenated composition. The hydrogenated composition was then oxidized for comparison with pure CHB. Oxidation was conducted using 0.1 wt % NHPI catalyst at 110° C. and 101 kPa (14.7 psi). As shown in FIG. 3, both compositions have similar activity indicating that the hydrogenation removes the olefins to a level where they have substantially no impact on the oxidation.

Example 5

SBB Production

One (1) gram of MCM-22 catalyst (65% MCM-22/35% alumina binder) was used for the alkylation of benzene with 2-butene. The catalyst was in the form of a 1.6 mm (⅟₁₆") diameter cylindrical extrudate, chopped to ⅟₁₆" length, and diluted with sand to 3 cm³ and loaded into an isothermal, down-flow, fixed-bed, tubular reactor having an outside diameter of 4.76 mm (³⁄₁₆"). The catalyst was dried at 150° C. and 1 atm with 100 cm³/min flowing nitroten for two hours. The nitrogen was turned off and benzene was fed to the reactor at 60 cm³/hr until the reactor pressure reached 300 psig. Benzene flow was then reduced to 7.63 cm³/hr (6.67 Weight Hourly Space Velocity (WHSV)). Butene feed (57.1% cis-butene, 37.8% trans-butene, 2.5% n-butane, 0.8% isobutene and 1-butene, and 1.8% other) was introduced from a syringe pump at 2.57 cc/hr (1.6 WHSV). Benzene/butene feed molar ratio was maintained at 3:1. The reactor temperature was adjusted to 160° C. 2-butene conversion was determined by measuring unreacted 2-butene (does butene need to be capitalized) relative to feed 2-butene. The catalyst was on stream for 4 days at 1.6 WHSV of butene with 97% 2-butene conversion, 2 days at 4.8 WHSV with 95% conversion, then 1 day at 7.2 WHSV with 86% conversion, and followed by 4 days at 1.6 WHSV with 97% conversion.

Example 6

Hydrotreatment of SBB

SBB (518 grams, 0.3864 mole), rhodium trichloride hydrate from Engelhard (0.52 g, 0.0025 mole) and trioctyl methyl ammonium chloride (Aliquat™ 336) from Aldrich Chemical Co. (0.52 grams, 0.001286 mole) were combined in a 100 cm³ Parr autoclave. The autoclave was pressurized to 345 KPa (50 psig) with hydrogen and the contents were stirred at room temperature for 19 hours. Hydrogen pressure was maintained at 345 KPa (50 psig). SBB was collected at a boiling point of 108° C./105 mm vacuum.

Example 7

Hydrotreatment of SBB

Same procedure as Example 6, except with the SBB from Example 5 (43.2 grams, 0.322 mole).

Example 8

Hydrotreatment of SBB

Same procedure as Example 6, except with the SBB from Example 5 (43.2 grams, 0.322 mole) and 1% palladium on alumina powder from Aldrich Chemical Co. (1.6 grams).

Example 9

Oxidation of SBB

Figure 8:
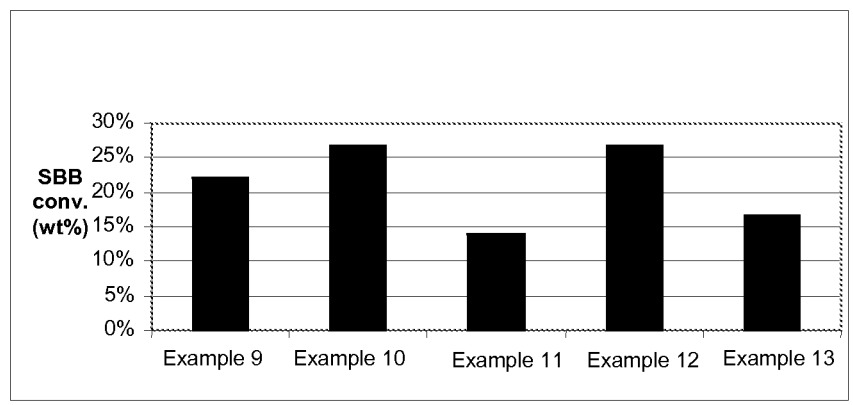
FIG. 8 illustrates SBB conversion of samples having varying amounts of olefins.

Pure SBB (518 grams, 0.3864 mole) and n-hydroxyphthalimide (NHPI) (0.185 grams, 0.001134 mole) from Aldrich Chemical Co were added into a 100 cm³ Parr autoclave. The contents were pressurized with nitrogen, followed by oxygen, to obtain 80:20 mixture at 1,480 kPa (215 psig) at room temperature. The contents of the autoclave were elevated to 115° C. and 1,720 kPa (250 psig). The oxygen concentration was maintained at approx. 20% throughout the six hour heating period by refilling with pure oxygen. At the completion of the run, the contents were cooled to room temperature and the product was removed from the autoclave and sampled using gas chromatography. See FIG. 8.

Example 10

Oxidation of SBB

The hydrogenation product of Example 6 was oxidized following the procedure of Example 9, except the following quantities were used: SBB (36.25 grams, 0.2705 mole) and NHPI (0.155 grams, 0.00095 mole). See FIG. 8.

Example 11

Oxidation of SBB

The hydrogenation product of Example 5 was oxidized following the procedure of Example 9, except the following quantities were used: SBB (36.25 grams, 0.2705 mole) and NHPI (0.155 grams, 0.00095 mole). See FIG. 8.

Example 12

Oxidation of SBB

The hydrogenation product of Example 7 was oxidized following the procedure of Example 9, except the following quantities were used: SBB (41 grams, 0.306 mole) and NHPI (0.176 grams, 0.00011 mole). See FIG. 8.

Example 13

Oxidation of SBB

The hydrogenation product of Example 8 was oxidized following the procedure of Example 9, except the following quantities were used: SBB (41 grams, 0.306 mole) and NHPI (0.176 grams, 0.00011 mole). See FIG. 8.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

In various embodiments, this invention relates to:
1. A hydrogenation process comprising:
    contacting a composition having:
        (i) greater than about 50 wt % of sec-butylbenzene, the wt % based upon total weight of the composition; and
        (ii) a hydrogenable component comprising a cyclic group;
    with hydrogen in the presence of a hydrogenation catalyst under hydrogenation conditions.
2. The process according to embodiment 1, wherein the cyclic group is aromatic.
3. The process according to embodiment 1, wherein the hydrogenable component comprises at least one of α-methylstyrene, α-ethylstyrene and butenyl-benzene.
4. The process according to embodiment 1, wherein the hydrogenable component is phenol.
5 The process according to embodiment 1, wherein the hydrogenable component is phenylbutanone.
6. The process of any of embodiments 1-5, wherein the composition has greater than about 1 wt % of the hydrogenable component, the wt % based upon total weight of the composition.
7. The process according to embodiment 1, wherein the contacting produces a second composition comprising less than about 1 wt % of the hydrogenable component, based upon the total weight of the second composition.
8. The process of any of embodiments 1-7, wherein the hydrogenation conditions comprise a temperature of about 10° C. to about 200° C.
9. The process of any of embodiments 1-8, wherein the hydrogenation conditions comprise a temperature of about 40° C. to about 80° C.
10. The process of any of embodiments 1-9, wherein the hydrogenation conditions comprise a temperature of about 65° C.
11. The process of any of embodiments 1-10, wherein the hydrogenation conditions comprise a pressure of about 0 kPa,g to about 3450 kPa,g.
12. The process of any of embodiments 1-11, wherein the hydrogenation conditions comprise a pressure of about 750 kPa,g to 1500 kPa,g.
13. The process of any of embodiments 1-12, wherein the hydrogenation catalyst comprises a hydrogenation component and a support.
14. The process of embodiment 13, wherein the hydrogenation component comprises at least one metal component selected from Groups 6 to 10 of the Periodic Table of Elements.
15. The process of embodiment 14, wherein the hydrogenation component comprises palladium.
16. The process of embodiment 15, wherein the hydrogenation catalyst comprises about 0.1 to about 10 wt % of the hydrogenation component, the wt % based upon total weight of the hydrogenation catalyst.

17. The process of embodiment 16, wherein the hydrogenation catalyst comprises about 0.3 wt % of the hydrogenation component, the wt % based upon total weight of the hydrogenation catalyst.

18. The process of embodiment 13, wherein the support comprises at least one of aluminum oxide, silica, silicate, aluminosilicate, carbon and a carbon nanotube.

19. The process of any of embodiments 1-18, wherein the process is continuous.

20. A hydrogenation process comprising:
contacting a composition comprising: (i) sec-butylbenzene; and (ii) a hydrogenable component comprising an aromatic ring, wherein the conversion is at least 50% more selective to sec-butylbenzene than butylcyclohexane.

21. A process for producing phenol comprising:
(a) alkylating benzene in the presence of a $C_4$ alkylating agent to form a composition having: (i) sec-butylbenzene; and (ii) a hydrogenable component comprising a cyclic ring;
(b) hydrogenating at least a portion of the hydrogenable component;
(c) oxidizing the sec-butylbenzene to form a oxidized composition comprising a peroxide; and
(d) cleaving the peroxide to form phenol and methyl ethyl ketone.

22. The process of embodiment 20, wherein the cleaving (d) forms a second hydrogenable component comprising at least one of an olefin, a ketone and phenol.

23. The process of embodiment 22, wherein the first hydrogenable component and the second hydrogenable component are the same or different.

24. The process of embodiment 22 or 23, further comprising:
(e) hydrogenating at least a portion of the second hydrogenable component.

25. The process of embodiment 24, wherein hydrogenating step (b) and hydrogenating step (e) are conducted in the same reactor.

26. The process of any of embodiments 21-25, further comprising dehydrogenating the methyl ethyl ketone to form at least some phenol.

27. The process of any of embodiments 21-26, wherein the oxidizing (c) is conducted in the presence of less than about 0.1 wt % phenol, the wt % based upon total weight of the oxidized composition.

28. The process of any of embodiments 21-27, wherein the hydrogenating (b) is conducted in the presence of a hydrogenation catalyst comprising a hydrogenation component and a support, wherein the hydrogenation component comprises at least one metal component selected from Groups 6 to 10 of the Periodic Table of and the support comprises at least one of aluminum oxide, silica, silicate, aluminosilicate and a carbon nanotube.

29. The process of embodiment 28, wherein the hydrogenation component comprises palladium.

30. The process of any of embodiments 21-29, wherein the hydrogenating (b) occurs at a temperature of about 10° C. to about 200° C. and a pressure of about 0 to about 3450 kPa,g.

The invention claimed is:
1. A hydrogenation process comprising:
(A) contacting a composition having:
(i) greater than about 50 wt % of cyclohexylbenzene, the wt % based upon total weight of the composition; and
(ii) a hydrogenable component comprising cyclohexenylbenzene;
with hydrogen in the presence of a hydrogenation catalyst under hydrogenation conditions.

2. The process of claim 1, wherein the hydrogenable component further comprises a compound having at least one of an unsaturated double bond, a hydroxyl group, and a carbonyl group.

3. The process of claim 1, wherein the hydrogenable component further comprises phenol.

4. The process of claim 3, wherein the contacting converts at least a portion of the phenol to cyclohexanone and/or cyclohexanol.

5. The process of claim 1, wherein the hydrogenable component comprises a ketone.

6. The process of claim 5, wherein the ketone is phenylcyclohexanone.

7. The process of claim 1, wherein the composition has greater than about 1 wt % of the hydrogenable component, the wt % based upon total weight of the composition.

8. The process of claim 1, wherein the contacting produces a second composition comprising less than about 1 wt % of the hydrogenable component, the wt % based upon the total weight of the second composition.

9. The process of claim 1, wherein the conversion of the hydrogenable component is at least 50% more selective to cyclohexylbenzene than to bicyclohexane.

10. The process of claim 1, wherein the contacting produces a second composition comprising less than 0.5 wt % of bicyclohexane, the wt % based upon total weight of the second composition.

11. The process of claim 1, wherein the hydrogenation conditions comprise a temperature of about 40° C. to about 80° C.

12. The process of claim 11, wherein the hydrogenation conditions comprise a temperature of about 65° C.

13. The process of claim 1, wherein the hydrogenation conditions comprise a pressure of about 750 kPa,g to 1500 kPa,g.

14. The process of claim 1, wherein the hydrogenation catalyst comprises a hydrogenation component and a support.

15. The process of claim 14, wherein the hydrogenation component comprises at least one metal component selected from Groups 6 to 10 of the Periodic Table of Elements.

16. The process of claim 14, wherein the hydrogenation component comprises palladium.

17. The process of claim 14, wherein the hydrogenation catalyst comprises about 0.1 to about 10 wt % of the hydrogenation component, the wt % based upon total weight of the hydrogenation catalyst.

18. A process for producing phenol comprising:
(a) hydroalkylating benzene to form a composition having:
(i) cyclohexylbenzene; and (ii) a first hydrogenable component comprising cyclohexenylbenzene;
(b) hydrogenating at least a portion of the first hydrogenable component;
(c) oxidizing the cyclohexylbenzene to form an oxidized composition comprising a hydroperoxide; and
(d) cleaving the hydroperoxide to form at least some phenol and cyclohexanone.

19. The process of claim 18, wherein the cleaving step (d) forms a second hydrogenable component comprising cyclohexenylbenzene.

20. The process of claim 19, further comprising:
(e) hydrogenating at least a portion of the second hydrogenable component.

21. The process of claim 20, wherein hydrogenating step (b) and hydrogenating step (e) are conducted in the same reactor.

22. The process of claim 18, wherein at least a portion of the cylcohexenylbenzene is converted into cyclohexylbenzene in step (b).

23. The process of claim 18, wherein the cleaving step (d) comprises:

(d1) obtaining a cleavage effluent comprising cyclohexylbenzene, phenol, cyclohexanone and cyclohexenylbenzene;

(d2) separating at least a portion of the cyclohexylbenzene and cyclohexenylbenzene from the cleavage effluent to obtain a recycle cyclohexylbenzene stream comprising cyclohexenylbenzene and at least 50 wt % of cyclohexylbenzene;

and the process further comprises:

(e) hydrogenating at least a portion of the recycle cyclohexylbenzene stream such that at least a portion of the cyclohexenylbenzene is converted to cyclohexylbenzene; and (f) recycling at least a portion of the hydrogenated recycle cyclohexylbenzene stream to step (c).

24. The process of claim 23, wherein the recycle cyclohexylbenzene stream further comprises phenol, and in step (e), at least a portion of the phenol contained in the recycle cyclohexylbenzene stream is converted to cyclohexanol.

25. The process of claim 1, wherein in step (ii), at least a portion of the cyclohexenylbenzene is converted to cyclohexylbenzene.

26. The process of claim 1, further comprising the following step (B) after step (A):

(B) oxidizing the composition such that at least a portion of the cyclohexylbenzene contained in the composition is converted to cyclohexylbenzene hydroperoxide.

* * * * *